(United States Patent)

Sciavolino et al.

[11] 4,382,085
[45] May 3, 1983

[54] 4"-EPI ERYTHROMYCIN A AND DERIVATIVES THEREOF AS USEFUL ANTIBACTERIAL AGENTS

[75] Inventors: Frank C. Sciavolino, Niantic; Mark A. Guadliana, Gales Ferry, both of Conn.

[73] Assignee: Pfizer Inc., New York, N.Y.

[21] Appl. No.: 353,547

[22] Filed: Mar. 1, 1982

[51] Int. Cl.³ .................. C07H 17/8; A61K 31/70
[52] U.S. Cl. ................................. 424/180; 536/7.2
[58] Field of Search ............... 424/180; 536/9, 7.2

[56] References Cited

U.S. PATENT DOCUMENTS 3,417,077  12/1968  Murphy et al. ............... 260/210
3,884,903  5/1975   Jones et al. ................. 260/210 E
4,150,220  4/1979   Sciavolino .................. 536/9

OTHER PUBLICATIONS

K. Gerzon, et al., J. Am. Chem. Soc., 78, 6396, (1956).
M. V. Sigal, et al., J. Am. Chem. Soc. 78, 388, (1956).

*Primary Examiner*—Johnnie R. Brown
*Attorney, Agent, or Firm*—Charles J. Knuth; Albert E. Frost; James M. McManus

[57] ABSTRACT

4"-Epi erythromycin A and 9-dihydro-4"-epi erythromycin A and derivatives thereof as useful antibacterial agents.

13 Claims, No Drawings

4"-EPI ERYTHROMYCIN A AND DERIVATIVES THEREOF AS USEFUL ANTIBACTERIAL AGENTS

FIELD OF THE INVENTION

This invention relates to novel semisynthetic antibiotic macrolides and in particular to 4"-epi erythromycin A and 11,12-carbonate ester thereof and to 9-dihydro-4"-epi erythromycin A and the 11,12-carbonate ester thereof.

DESCRIPTION OF THE ART

Erythromycin is an antibiotic formed during the culturing of a strain of *Streptomyces erythreus* in a suitable medium as taught in U.S. Pat. No. 2,653,899. Erythromycin, which is produced in two forms, A and B, is represented by the following structure:

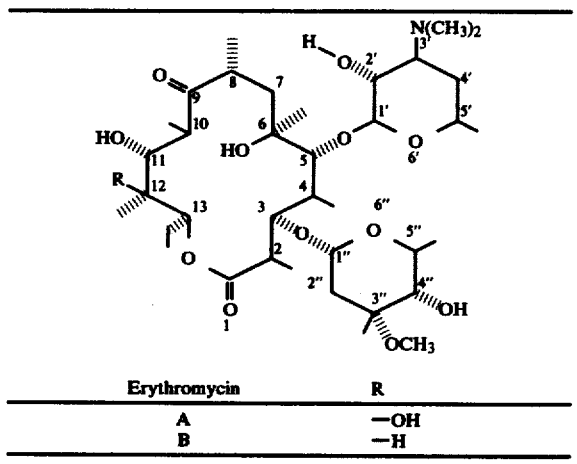

| Erythromycin | R |
|---|---|
| A | —OH |
| B | —H |

Numerous derivatives of erythromycin have been prepared in an effort to modify its biological or pharmacodynamic properties.

U.S. Pat. No. 3,417,077 describes the reaction product of erythromycin and ethylene carbonate as a very active antibacterial agent. U.S. Pat. No. 3,884,903 discloses 4"-deoxy-4"-oxo-erythromycin A and B derivatives as being useful as antibiotics, and U.S. Pat. No. 4,150,220 describes a new synthesis for 4"-oxo-erythromycin A and its use as an intermediate leading to antibacterial agents. 9-Dihydroerythromycin A was reported by K. Gerzon, et. al., *J. Am. Chem. Soc.*, 78, 6396 (1956) and M. V. Sigal, et. al., *J. Am. Chem. Soc.*, 78, 388 (1956).

SUMMARY OF THE INVENTION

The semisynthetic macrolide antibacterial agents of the present invention are represented by the formula

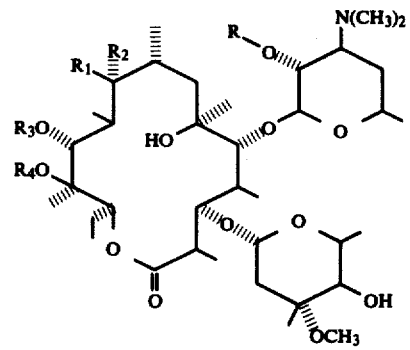

and the pharmaceutically acceptable acid addition salts thereof, wherein R is hydrogen, alkanoyl of two to three carbon atoms or ethyl succinyl; $R_1$ and $R_2$ when considered separately are, respectively, hydroxy and hydrogen; $R_1$ and $R_2$ when considered together are an oxo group; $R_3$ and $R_4$ when considered separately are each hydrogen; and $R_3$ and $R_4$ when considered together are $>C=O$.

A preferred group of compounds are those wherein $R_1$ and $R_2$ are an oxo group. Especially preferred within said group are 4"-epi erythromycin A, 2'-acetyl-4"-epi erythromycin A, 4"-epi erythromycin A 11,12-carbonate ester and 2'-acetyl-4"-epi erythromycin A 11,12-carbonate ester.

A second group of preferred compounds are those wherein $R_1$ is hydroxy, $R_2$ is hydrogen and $R_3$ and $R_4$ together are $>C=O$. Especially preferred within this group are 9-dihydro-4"-epi erythromycin A 11,12-carbonate ester and 9-dihydro-2'-acetyl-4"-epi erythromycin A 11,12-carbonate ester.

A third group of preferred compounds are those wherein $R_1$ is hydroxy, $R_2$ is hydrogen and $R_3$ and $R_4$ are each hydrogen. Especially preferred within said class are 9-dihydro-4"-epi erythromycin A and 9-dihydro-2'-acetyl-4"-epi erythromycin A.

As one skilled in the art will appreciate, erythromycin macrolides having a substituent at the 11,12-hydroxy groups can readily exist in the hemi-ketal form, said form being in equilibrium with the keto form depicted as follows:

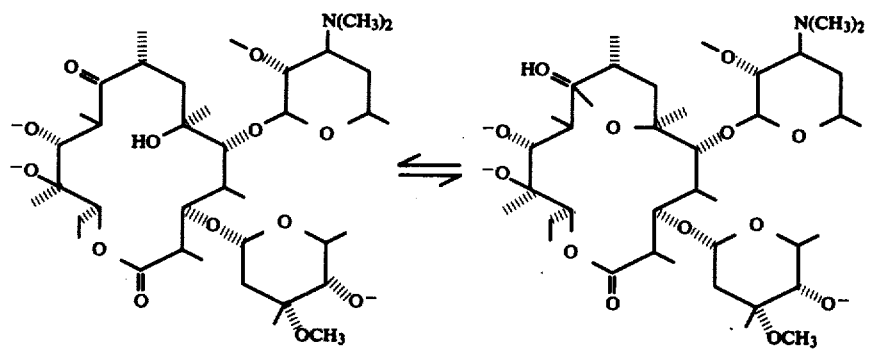

For convenience, all such structures which have the potential to exist in said forms are written and named in the keto form, although both forms, where they exist, are fully contemplated by the present invention.

DETAILED DESCRIPTION OF THE INVENTION

4''-Epi erythromycin A (R=H; $R_1+R_2$=O; and $R_3,R_4$=H) is readily prepared by the hydrogenation of 4''-deoxy-4''-oxo-erythromycin A (U.S. Pat. No. 4,150,220) in the presence of a Raney nickel or noble metal catalyst in a reaction-inert solvent. By a reaction-inert solvent is meant one which solubilizes the appropriate reagents but does not react to any appreciable extent with either the starting reagents or final product. Solvents or mixtures thereof which are suitable for this reaction include lower alkanols, such as isopropanol and ethanol.

The reaction is conveniently conducted at ambient temperatures, requiring about 4–6 hours for substantial completion. It is frequently preferred to allow the reaction to proceed overnight.

The ratio of reactant to Raney nickel or noble metal catalyst is not critical and it is preferred that equal weight amounts of Raney nickel or noble metal catalyst and macrolide be employed. Regarding the hydrogen reactant, an initial pressure of 50 psi efficiently produces the desired reduction without formation of by-products in substantial amounts.

The product can be isolated by conventional means. One preferred method comprises filtration of the spent catalyst, concentration of the filtrate and precipitation of the product with water.

Compounds of the present invention wherein R=H, $R_1+R_2$=O and $R_3+R_4$=>C=O can be synthesized by reacting the corresponding 4''-epi erythromycin with ethylene carbonate in a reaction inert solvent.

The reaction, which can be carried out in lower alkyl alkanoates such as ethyl acetate, is usually conducted at reflux temperatures for about 3–6 hours.

It is preferred that a three to five-fold weight excess of ethylene carbonate to macrolide be employed to ensure completion of the reaction. The excess can be employed at the beginning of the reaction or can be added in divided portions throughout the reaction period.

On completion of the reaction, water is added and the product extracted in the reaction solvent. The solvent is subsequently removed and the residual product purified by conventional means.

An alternate method for preparing 4''-epi erythromycin A 11,12-carbonate ester employs reduction of the corresponding 4''-deoxy-4''-oxo-erythromycin A 11,12-carbonate (U.S. Pat. No. 4,150,220) using a Raney nickel or noble metal catalyst and hydrogen in a manner exactly the same as that previously described for the reduction of 4''-deoxy-4''-oxo-erythromycin A.

Acylation of 4''-epi erythromycin A or 4''-epi erythromycin A 11,12-carbonate ester leads to 2'-acyl derivatives thereof. Experimentally, equimolar amounts of the alkanoic anhydride, plus about a 10% excess, and the appropriate macrolide are contacted in a reaction-inert solvent.

Preferred solvents include water immiscible, aprotic solvents such as methylene chloride, toluene, ethyl acetate and chloroform.

The reaction is conducted at room temperature, but can be cooled to 0° C. or heated to reflux. When run at ambient temperatures, the reaction is substantially complete in 5–7 hours.

On completion of the reaction, water is added and the product subsequently isolated from the organic phase and purified.

The acylation of the 2'-hydroxy group can also be carried out with an acyl halide such as the chloride or bromide. When such an acyl halide is employed as the acylating agent, it is preferred that at least an equivalent amount of an acid scavenger be added such as sodium bicarbonate. Further, when the acylating agent is an acid halide, the preferred solvent is acetone, and on completion of the reaction the mixture is poured into a water-water immiscible solvent mixture and the product isolated from the organic layer.

9-Dihydro-4''-epi erythromycin A is prepared by reduction of 4''-deoxy-4''-oxo-erythromycin A (U.S. Pat. No. 4,150,220) with Raney nickel. The reaction is carried out at ambient temperatures at an initial pressure of about 1400 psi in a reaction-inert solvent. Under these reaction conditions the reduction is usually complete in 12–14 hours, but can be conveniently conducted overnight to ensure completion. The preferred solvents are lower-alkanols, such as ethanol, methanol or isopropanol. The ratio of Raney nickel to macrolide is about 5 to 1 on a weight basis. On completion of the reaction, the catalyst is filtered and the filtrate concentrated to give the desired product which may be purified by conventional means.

9-Dihydro-4''-epi erythromycin A 11,12-carbonate is conveniently prepared by treatment of 9-dihydro-4''-epi erythromycin A with ethylene carbonate in a reaction-inert solvent such as toluene or benzene. As in the preparation of 11,12-carbonate esters of 4''-epi erythromycin A, it is preferred that a three to five-fold weight excess of ethylene carbonate to macrolide be employed to ensure completion of the reaction. The excess may be added at the beginning of the reaction or in divided portions during the reaction period. The reaction is conducted at about 40°–60° C. with a preferred reaction temperature of about 55° C. At such a reaction temperature the reaction is substantially complete in about 4–5 hours. The product can be isolated by treating the reaction with water, acidifying with acid to dissolve the macrolide in the aqueous phase followed by basifying after any undesired by-products or excess ethylene carbonate have been removed.

An alternate method for the synthesis of 9-dihydro-4''-epi erythromycin A 11,12-carbonate ester is the hydride reduction of 4''-epi erythromycin A 11,12-carbonate ester. Experimentally, the macrolide is reacted with a ten-fold molar excess of sodium borohydride in a solvent comprised of a lower alkanol such as ethanol and water in a volume ratio of 10 to 1. The reaction can be conveniently carried out at room temperature, requiring a reaction time of 1–2 hours. On completion, the reaction mixture is added to a water-water immiscible solvent mixture, such as water-methylene chloride, and the product subsequently isolated from the organic phase. Acylation of the 2'-hydroxy group of 9-dihydro-4''-epi erythromycin A and 9-dihydro-4''-epi erythromycin A 11,12-carbonate ester is achieved by the same procedure as previously described for the acylation of 4''-epi erythromycin A and its 11,12-carbonate ester.

The reagents for the process leading to the compounds of the present invention are all known in the art, are commercially available or are described herein. The preparation of the 4''-deoxy-4''-oxo-erythromycin A macrolides are reported in U.S. Pat. No. 4,150,220. Preferred among these compounds because of their antibacterial utility are 4″-epi erythromycin A, 2′-acetyl-4″-epi erythromycin A, 4″-epi erythromycin A 11,12-carbonate ester, 2′-acetyl-4″-epi erythromycin A 11,12-carbonate ester, 9-dihydro-4″-epi erythromycin A 11,12-carbonate ester, 9-dihydro-2′-acetyl-4″-epi erythromycin A, 9-dihydro-4″-epi erythromycin A, 9-dihydro-2′-acetyl-4″-epi erythromycin A.

In the utilization of the chemotherapeutic activity of those compounds of the present invention which form salts, it is preferred, of course, to use pharmaceutically acceptable salts. Although water-insolubility, high toxicity, or lack of crystalline nature may make some particular salt species unsuitable or less desirable for use as such in a given pharmaceutical application, the water insoluble or toxic salts can be converted to the corresponding pharmaceutically acceptable bases by decomposition of the salt as described above, or alternately they can be converted to any desired pharmaceutically acceptable acid addition salt.

Examples of acids which provide pharmaceutically acceptable anions are hydrochloric, hydrobromic, hydroiodic, nitric, sulfuric, or sulfurous, phosphoric, acetic, lactic, citric, tartaric, succinic, maleic, gluconic and aspartic acids.

The novel erythromycins described herein exhibit in vitro activity against a variety of Gram-positive microorganisms such as *Staphylococcus aureus* and *Streptococcus pyogenes* and against certain Gram-negative microorganisms such as those of spherical or ellipsoidal shape (cocci). Their activity is readily demonstrated by in vitro tests against various microorganisms in a brain-heart infusion medium by the usual two-fold serial dilution technique. Their in vitro activity renders them useful for topical application in the form of ointments, creams and the like; for sterilization purposes, e.g., sickroom utensils; and as industrial antimicrobials, for example, in water treatment, slime control, paint and wood preservation.

For in vitro use, e.g., for topical application, it will often be convenient to compound the selected product with a pharmaceutically-acceptable carrier such as vegetable or mineral oil or an emollient cream. Similarly, they may be dissolved or dispersed in liquid carriers or solvents, such as water, alcohol, glycols or mixtures thereof or other pharmaceutically-acceptable inert media; that is, media which have no harmful effect on the active ingredient. For such purposes, it will generally be acceptable to employ concentrations of active ingredients of from about 0.01 percent to about 10 percent by weight based on total composition.

Additionally, many compounds of this invention are active versus Gram-positive and certain Gram-negative microorganisms in vivo such as *Pasteurella multocida* and *Neisseria sicca* via the oral and/or parenteral routes of administration in animals, including man. Their in vivo activity is more limited as regards susceptible organisms and is determined by the usual procedure which comprises treating mice of substantially uniform weight with the test organism and subsequently treating them orally or subcutaneously with the test compound. In practice, the mice, e.g. 10, are given an intraperitoneal inoculation of suitably diluted cultures containing approximately 1 to 10 times the $LD_{100}$ (the lowest concentration of organisms required to produce 100% deaths). Control tests are simultaneously run in which mice receive inoculum of lower dilutions as a check on possible variation in virulence of the test organism. The test compound is administered 0.5 hour postinoculation, and is repeated 4, 24 and 48 hours later. Surviving mice are held for four days after the last treatment and the number of survivors is noted.

When used in vivo, these novel compounds can be administered orally or parenterally, e.g., by subcutaneous or intramuscular injection, at a dosage of from about 25 mg/kg to about 200 mg/kg of body weight per day. The favored dosage range is from about 150 mg/kg to about 200 mg/kg of body weight per day. Vehicles suitable for parenteral injection may be either aqueous such as water, isotonic saline, isotonic dextrose, Ringer's solution, or non-aqueous such as fatty oils of vegetable origin (cotton seed, peanut oil, corn, sesame), dimethylsulfoxide and other non-aqueous vehicles which will not interfere with therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents, for example, propylene glycol, diethyl carbonate, glycerol, sorbitol, etc.; buffering agents, hyaluronidase, local anesthetics and inorganic salts to afford desirable pharmacological properties. These compounds may also be combined with various pharmaceutically-acceptable inert carriers including solid diluents, aqueous vehicles, non-toxic organic solvents in the form of capsules, tablets, lozenges, troches, dry mixes, suspensions, solutions, elixirs and parenteral solutions or suspensions. In general, the compounds are used in various dosage forms at concentration levels ranging from about 0.5 percent to about 90 percent by weight of the total composition.

The following examples are provided solely for the purpose of illustration and are not to be construed as limitations of this invention, many variations of which are possible without departing from the spirit or scope thereof.

EXAMPLE 1

4″-Epi erythromycin A 11,12-carbonate ester

A mixture of 109 g. of Raney nickel sludge and 109 g. of 4″-deoxy-4″-oxo-erythromycin A 11,12-carbonate ester (U.S. Pat. No. 4,150,220) in 1 liter of absolute ethanol was shaken in a hydrogen atmosphere at 50 psi overnight at room temperature. The solids were filtered through super-cel and the filtrate concentrated in vacuo to 550–600 ml. The concentrated filtrate was warmed on a steam bath and treated with 600 ml of warm water. The solution was allowed to stir at room temperature for 1.5 hours and the crystallized product filtered and oven dried at 50° C. overnight, 59.8 g. The product was purified by recrystallization from ethanol-water, 49.1 g., m.p. 141°–143° C. The NMR spectrum (CDCl$_3$) showed absorption at 3.69 (2H, q), 3.29 (3H, s), 2.27 (6H, s) and 1.58 (3H, s) ppm.

EXAMPLE 2

4″-Epi erythromycin A 11,12-carbonate ester

A. 4″-epi erythromycin A

A suspension of 100 g. of Raney nickel sludge in 1 liter of absolute ethanol containing 100 g. of 4″-deoxy-4″-oxo-erythromycin A (U.S. Pat. No. 4,150,220) was shaken in a hydrogen atmosphere overnight at room temperature at 50 psi. The spent catalyst was filtered through super-cel and the filtrate concentrated in vacuo to 300 ml. Water (700 ml) was added to the concentrated filtrate and the resulting milky solution warmed on a steam bath. A small amount of ethanol was added to prevent gumming of the product as it precipitated from solution. After stirring for 2 hours at room temperature the product was filtered and dried, 57.6 g, and the filtrate concentrated in vacuo to the haze point. The mixture was allowed to stir for one hour and was filtered and dried, 21.4 g. The resulting crops were combined, m.p. 141°–144° C. The NMR spectrum (CDCl$_3$) showed absorption at 3.3 (3H, s) 2.3 (6H, s) and 1.4 (3H, s) ppm.

In a similar manner, 200 mg of 4"-deoxy-4"-oxo-erythromycin A and 600 mg of 10% palladium-on-charcoal in 30 ml of methanol when shaken in a hydrogen atmosphere for four hours gave, on a similar work-up, 118 mg of 4"-epi erythromycin A.

B. 4"-epi erythromycin A 11,12-carbonate ester

A mixture comprised of 10 g of 4" epi erythromycin A, 20 g of ethylene carbonate and 5 g of potassium carbonate in 100 ml of ethyl acetate was heated to reflux 3.5 hours. An additional 10 g of ethylene carbonate was added and heating continued for 2 hours. The reaction mixture was cooled to room temperature and poured into 100 ml of water with stirring. The ethyl acetate layer was separated, washed successively with water (2×100 ml) and a saturated brine solution (1×100 ml) and dried over sodium sulfate. Removal of the solvent gave the product as a viscous liquid. The residue was recrystallized from isopropyl etherdiethyl ether, 2.54 g, isopropanol and then ethanol-water, 896 mg. The product was identical in every respect with that prepared in Example 1.

EXAMPLE 3

2'-Acetyl-4"-epi erythromycin A 11,12-carbonate ester

To a stirring solution of 1.3 g of 4"-epi erythromycin A 11,12-carbonate ester in 20 ml of methylene chloride was added 0.167 ml of acetic anhydride, and the resulting reaction mixture allowed to stir at room temperature for 6 hours. The reaction was poured into a saturated sodium bicarbonate solution. The organic phase was washed with water and a saturated brine solution, and dried over sodium sulfate. Removal of the solvent in vacuo gave the product as a white foam, 1.28 g. Recrystallization from isopropyl ether gave 904 mg of the pure product, m.p. 212°–214° C. The NMR spectrum (CDCl$_3$) showed absorption at 3.29 (3H, s), 2.25 (6H, s), 2.03 (3H, s) and 1.59 (3H, s) ppm.

EXAMPLE 4

2'-Propionyl-4"-epi erythromycin A 11,12-carbonate ester

A solution of 1.3 g of 4"-epi erythromycin A 11,12-carbonate ester and 0.227 ml of propionic anhydride in 20 ml of methylene chloride was allowed to stir at room temperature for 6 hours. The reaction was poured into a saturated sodium bicarbonate solution and the organic phase separated and washed with water and a saturated brine solution. The organic phase was dried with sodium sulfate and concentrated in vacuo to a white foam, 1.3 g. The product was recrystallized from acetone-water, 888 mg, m.p. 209°–213° C. The NMR spectrum (CDCl$_3$) showed absorption at 3.32 (3H, s), 2.24 (6H, s) and 1.59 (3H, s) ppm.

EXAMPLE 5

2'-(2-ethoxycarbonylpropionyl)-4"-epi erythromycin A 11,12-carbonate ester

A mixture of 1.3 g of 4"-epi erythromycin A 11,12-carbonate ester, 0.344 ml of ethyl succinyl chloride and 1 g of sodium bicarbonate in 15 ml of acetone was allowed to stir at room temperature for 3 hours. The mixture was poured into water-methylene chloride. The organic phase was separated and washed with water and a saturated brine solution. The organic phase was dried over sodium sulfate and concentrated under vacuum to a white foam, 1.4 g. The product was recrystallized from isopropyl ether, 915 mg, m.p. 179°–182° C. The NMR spectrum (CDCl$_3$) showed absorption at 3.3 (3H, s), 2.61 (4H, s), 2.22 (6H, s) and 1.57 (3H, s) ppm.

EXAMPLE 6

2'-Acetyl-4"-epi erythromycin A

To a solution of 14 g of 4"-epi erythromycin A in 100 ml of methylene chloride was added 1.75 ml of acetic anhydride and the reaction mixture allowed to stir at room temperature for 2 hours. The reaction was poured into water and the pH adjusted to 9 with solid sodium bicarbonate. The organic phase was separated, washed with water and a saturated brine solution and dried over sodium sulfate. Removal of the solvent in vacuo gave 13.6 g of crude product which was recrystallized from hexane-ethyl acetate, 11.5 g. The NMR spectrum (CDCl$_3$) showed absorption at 3.3 (3H, s), 2.3 (6H, s), 2.0 (3H, s) and 1.4 (3H, s) ppm.

EXAMPLE 7

2'-Propionyl-4"-epi erythromycin A

To a suspension of 1.5 g of 4"-epi erythromycin A in 15 ml of acetone was added 0.34 ml of propionic anhydride and the reaction mixture allowed to stir at room temperature overnight. The reaction was poured into methylene chloride and dilute sodium bicarbonate. The organic phase was separated and washed with water and a saturated brine solution. After drying the organic phase over sodium sulfate, the solvent was removed in vacuo to give 1.52 g of the product. Purification was by recrystallization from acetone-water, 657 mg, m.p. 192°–195° C. The NMR spectrum (CDCl$_3$) showed absorption at 3.3 (3H, s) 2.3 (6H, s) and 1.4 (3H, s) ppm.

EXAMPLE 8

2'-(2-Ethoxycarbonylpropionyl)-4"-epi erythromycin A

To a suspension of 1.5 g of 4"-epi erythromycin A and 1.0 g of sodium bicarbonate in 15 ml of acetone was added 0.32 ml of ethyl succinyl chloride and the reaction mixture allowed to stir at room temperature for 4 hours. An additional 0.106 ml of the acid chloride was added and stirring continued for one hour. The reaction was added to methylene chloride and dilute sodium bicarbonate, the organic phase separated, washed with water and a saturated brine solution and dried over sodium sulfate. Removal of the solvent under vacuum gave 1.7 g of the crude product which was recrystallized from isopropyl ether, 639 mg, m.p. 123°–127.5° C. The NMR spectrum (CDCl$_3$) showed absorption at 3.3 (3H, s), 2.6 (4H, s), 2.2 (6H, s) and 1.4 (3H, s) ppm.

EXAMPLE 9

9-Dihydro-4''-epi erythromycin A 11,12-carbonate ester

To a stirring solution of 500 mg of 4''-epi erythromycin A 11,12-carbonate ester (Example 1) in 10 ml of ethanol and 1 ml of water at room temperature and under a nitrogen atmosphere was added 249 mg of sodium borohydride. The reaction was allowed to stir for 1.5 hours and was then poured into a stirring mixture of water-methylene chloride and the pH adjusted to 2.5. After 10 minutes the pH was adjusted to 11 and the organic phase separated, washed with water and a saturated brine solution and dried over sodium sulfate. The solvent was removed in vacuo to yield the crude product, 415 mg, as a white foam. The product was purified by chromatographing on 36 g of silica gel 60 (230–400 mesh) using chloroform-methanol-ammonium hydroxide (97:3:0.03; v:v:v) as the eluent and taking 7 ml fractions. At fraction 55 the ratio of the eluent was changed to 90:10:0.03 and fractions 72–100 were collected and combined. Removal of the solvent yielded the pure product, 209 mg. The NMR spectrum (CDCl$_3$) showed absorption at 3.26 (3H, s), 2.30 (6H, s) and 1.46 (3H, s) ppm.

EXAMPLE 10

9-Dihydro-4''-epi erythromycin A 11,12-carbonate ester

A. 9-dihydro-4''-epi erythromycin A

A slurry of 50 g (68.3 mmoles) of 4''-deoxy-4''-oxo-erythromycin A (U.S. Pat. No. 4,150,220) and 250 g of Raney nickel in 500 ml of ethanol was shaken in a hydrogen atmosphere at an initial pressure of 1400 psi at room temperature overnight. The mixture was filtered through super-cel and the filtrate concentrated under vacuum to a colorless solid, which was purified by recrystallization from acetone-water, 37 g, m.p. 139°–143° C. The NMR spectrum (CDCl$_3$) showed absorption at 3.31 (3H, s) and 2.31 (6H, s) ppm.

B. 9-dihydro-4''-epi erythromycin A 11,12-carbonate ester

In a 2 liter flask fitted with a mechanical stirrer and thermometer was added 60 g of 9-dihydro-4''-epi erythromycin A, 300 g of ethylene carbonate, 150 g of potassium carbonate and 600 ml of toluene, and the mixture stirred at 55° C. in an oil bath for 4.5 hours. The cooled reaction mixture was poured into 600 ml of water and the organic phase separated and added to 600 ml of fresh water. The pH was adjusted to 2.5 and the organic phase separated and discarded. The aqueous layer was washed with 600 ml of toluene and was combined with 600 ml of methylene chloride and the pH of the mixture adjusted to 9.5. The organic layer was separated, washed with water (2×400 ml) and a saturated brine solution (1×400 ml) and dried over sodium sulfate. Removal of the solvent under vacuum gave 98 g of the crude product which was purified by recrystallization from ethanol-water, 28.5 g, m.p. 131°–135° C. The product was identical in every respect to that obtained in Example 9. The NMR spectrum (CDCl$_3$) showed absorption at 3.26 (3H, s), 2.30 (6H, s) and 1.46 (3H, s) ppm.

EXAMPLE 11

9-Dihydro-2'-acetyl-4''-epi erythromycin A 11,12-carbonate ester

To a solution of 1.5 g of 9-dihydro-4''-epi erythromycin A 11,12-carbonate ester in 15 ml of methylene chloride was added 0.214 ml of acetic anhydride and the reaction mixture allowed to stir at room temperature for 6 hours. The reaction was poured into 25 ml of water and the pH adjusted to 9.5. The organic phase was separated, washed with water and a saturated bring solution and dried over sodium sulfate. Removal of the solvent in vacuo gave 1.4 g of the product. The NMR spectrum (CDCl$_3$) showed absorption at 3.29 (3H, s), 2.25 (6H, s), 2.0 (3H, s), 1.43 (3H, s) ppm.

EXAMPLE 12

9-Dihydro-2'-propionyl-4''-epi erythromycin A 11,12-carbonate ester

In a manner similar to Example 11, 1.5 g of 9-dihydro-4''-epi erythromycin A 11,12-carbonate ester and 0.306 ml of propionic anhydride in 15 ml of methylene chloride gave, after a reaction time of 5 hours, 1.41 g of the desired product. The NMR spectrum (CDCl$_3$) showed absorption at 3.32 (3H, s), 2.27 (6H, s) and 1.46 (3H, s) ppm.

EXAMPLE 13

9-Dihydro-2'-(2-ethoxycarbonylpropionyl)-4''-epi erythromycin A 11,12-carbonate ester To a stirring solution of 1.5 g of 9-dihydro-4''-epi erythromycin A 11,12-carbonate in 15 ml of acetone was added 1 g of sodium bicarbonate followed by 0.421 ml of ethyl succinyl chloride and the mixture allowed to stir at room temperature for 6.5 hours. The mixture was poured into a mixture of water-methylene chloride and the pH adjusted to 9.5. The organic phase was separated, washed with water and a saturated brine solution and dried over sodium sulfate. Removal of the solvent under vacuum gave 1.6 g of the desired product. The NMR spectrum (CDCl$_3$) showed absorption at 3.31 (3H, s), 2.62 (4H, s), 2.27 (6H, s) and 1.47 (3H, s) ppm.

We claim:

1. A compound selected from the group consisting of a macrolide antibiotic of the formula:

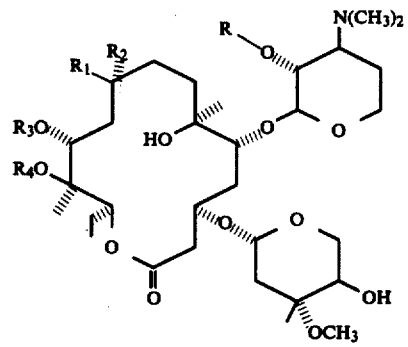

and the pharmaceutically acceptable acid addition salts thereof, wherein R is selected from the group consisting of hydrogen, alkanoyl having from two to three carbon atoms and ethyl succinyl; $R_1$ and $R_2$ when considered separately are, respectively, hydroxy and hydrogen; $R_1$ and $R_2$ when considered together are an oxo group; $R_3$ and $R_4$ when considered separately are each hydrogen; and $R_3$ and $R_4$ when considered together are $>C=O$.

2. A compound of claim 1 wherein $R_1$ and $R_2$ when considered together are an oxo group.

3. The compound of claim 2 wherein R is hydrogen and $R_3$ and $R_4$ are each hydrogen.

4. The compound of claim 2 wherein R is acetyl and $R_3$ and $R_4$ are each hydrogen.

5. The compound of claim 2 wherein R is hydrogen and $R_3$ and $R_4$ together are $>C=O$.

6. The compound of claim 2 wherein R is acetyl and $R_3$ and $R_4$ together are $>C=O$.

7. A compound of claim 1 wherein $R_1$ is hydroxy, $R_2$ is hydrogen and $R_3$ and $R_4$ together are $>C=C$.

8. The compound of claim 7 wherein R is hydrogen.

9. The compound of claim 7 wherein R is acetyl.

10. A compound of claim 1 wherein $R_1$ is hydroxy, $R_2$ is hydrogen and $R_3$ and $R_4$ are each hydrogen.

11. The compound of claim 10 wherein R is hydrogen.

12. The compound of claim 10 wherein R is acetyl.

13. An antibacterial pharmaceutical composition comprising from about 0.5 to about 90 percent by weight of the total composition a compound as claimed in claim 1 and a pharmaceutical carrier.

* * * * *